US009440897B2

(12) United States Patent
Lange et al.

(10) Patent No.: US 9,440,897 B2
(45) Date of Patent: Sep. 13, 2016

(54) PROCESS FOR THE PREPARATION OF MONOETHYLENE GLYCOL

(71) Applicant: SHELL OIL COMPANY, Houston, TX (US)

(72) Inventors: Jean Paul Andre Marie Joseph Gishlain Lange, Amsterdam (NL); Pieter Huizenga, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 14/786,306

(22) PCT Filed: Apr. 23, 2014

(86) PCT No.: PCT/EP2014/058273
§ 371 (c)(1),
(2) Date: Oct. 22, 2015

(87) PCT Pub. No.: WO2014/173973
PCT Pub. Date: Oct. 30, 2014

(65) Prior Publication Data
US 2016/0096789 A1 Apr. 7, 2016

(30) Foreign Application Priority Data
Apr. 26, 2013 (EP) .................... 13165644

(51) Int. Cl.
C08G 63/66 (2006.01)
C07C 29/132 (2006.01)
C12P 19/02 (2006.01)
C13K 3/00 (2006.01)
C07H 1/00 (2006.01)
C07H 3/02 (2006.01)
C12P 19/24 (2006.01)
C07C 51/00 (2006.01)
A23L 1/236 (2006.01)
A23L 2/60 (2006.01)
C07D 307/50 (2006.01)
C07D 307/68 (2006.01)
C07H 1/08 (2006.01)
C08G 63/16 (2006.01)
C08G 63/00 (2006.01)

(52) U.S. Cl.
CPC ............ *C07C 29/132* (2013.01); *A23L 1/2364* (2013.01); *A23L 2/60* (2013.01); *C07C 51/00* (2013.01); *C07D 307/50* (2013.01); *C07D 307/68* (2013.01); *C07H 1/00* (2013.01); *C07H 1/08* (2013.01); *C07H 3/02* (2013.01); *C08G 63/16* (2013.01); *C12P 19/02* (2013.01); *C12P 19/24* (2013.01); *C13K 3/00* (2013.01); *A23V 2002/00* (2013.01)

(58) Field of Classification Search
CPC ................ C08G 63/20; C08G 63/66

USPC ...................... 528/300, 307, 308.3
See application file for complete search history.

(56) References Cited

FOREIGN PATENT DOCUMENTS

| CN | 103731258 | 4/2014 |
|---|---|---|
| EP | 2033958 | 3/2009 |
| JP | 2013060379 | 4/2013 |
| WO | 2009030504 | 3/2009 |
| WO | 2009030508 | 3/2009 |
| WO | 2013015955 | 1/2013 |

OTHER PUBLICATIONS

Ji, Na, et. al.: Direct Catalytic Conversion of Cellulose into Ethylene Glycol Using Nickel-Promoted Tungsten Carbide Catalysts, Biomass Conversion, Angew. Chem. int. Ed. 2008, 47, pp. 8510-8513.
Rearick, D. Eugene, et al.: Simulated moving-bed technology in the sweetener industry, Chemtech, 1997, 27(9), pp. 36-.
van Putten, Robert-Jan, et al.: Hydroxymethylfurfural, A versatile platform chemical made from renewable resources, Chem. Reviews, 2013, 113, pp. 1499-1597.
Kuster, B.F.M., 5-Hydroxymethylfurfural (HMF) A review focussing on its manufacture, Starchlstarke, 1990, 42 (8), pp. 314-321.
Moliner, Manuel, et al.: Tin-containing zeolites are highly active catalysts for the isomerization of glucose in water, Proc. Natl. Acad. Sci. USA, 2010 107 (14), pp. 6164-6168.
Makkee, M., et al.: Glucose-isomerase-catalyzed D-glucose-D-fructose interconversion: mecanism and reactive species, Recuell, Journal of the Royal Netherlands Chemical Society, 1984, 103, pp. 361-364.
Mendicino, Joseph F.: Effect of Borate on the alkali-catalyzed isomerization of sugars, J. Am. Chem. Soc., 1960, 82, pp. 4975-4979.
Takagaki, Atsushi, et al.: A one-pot reaction for biorefinery: combination of solid acid and base catalysts for direct production of 5-hydroxymethylfurfural from saccharides, Chemical Communications, No. 41, Jan. 1, 2009, p. 6276, XP055015326.
Saxena, Utkarsh, et al.: Effect of Catalyst Constituents on (Ni, Mo, and Cu)/Kieselguhr-Catalyzed Sucrose Hydrogenolysis, Industrial & Engineering Chemistry Research, vol. 44, No. 5, Mar. 1, 2005, pp. 1466-1473, XP055032208.
Rosatella, A.A., et al.: 5-Hydroxymethylfurfural as a building block platform: biological properties, synthesis and synthetic applications, Green Chemistry, vol. 13, Dec. 15, 2010, pp. 754-793, XP002714416.
International Search Report dated May 6, 2014 of PCT/EP2014/058273 filed Apr. 23, 2014.

*Primary Examiner* — Terressa Boykin

(57) ABSTRACT

The invention provides a process for the preparation of monoethylene glycol from sucrose comprising the steps of: i) hydrolyzing sucrose to form a reaction product stream comprising glucose and fructose; ii) separating the reaction product stream comprising glucose and fructose into a fructose or fructose derivative rich stream and a glucose rich stream; and iii) contacting the glucose rich stream with hydrogen in a reactor in the presence of a solvent and a catalyst system with catalytic hydrogenation abilities to produce a product stream comprising monoethylene glycol.

10 Claims, 2 Drawing Sheets

US 9,440,897 B2

PROCESS FOR THE PREPARATION OF MONOETHYLENE GLYCOL

PRIORITY CLAIM

The present Application is a National Stage §371 application of PCT/EP2014/058273, filed Apr. 23, 2014, which claims priority from European Patent Application 13165644.9 filed Apr. 26, 2014, each of which are hereby incorporated by reference in their entirety.

FIELD OF THE INVENTION

The present invention relates to a process for the preparation of monoethylene glycol.

BACKGROUND OF THE INVENTION

Ethylene glycol is a valuable material with a multitude of commercial applications. Monoethylene glycol (MEG) is used as a raw material in the manufacture of polyester fibres, polyethylene terephthalate (PET) plastics and resins. It is also incorporated into automobile antifreeze liquids.

In a typical industrial process, MEG is prepared in a two-step process. In the first step, ethylene is converted to ethylene oxide by reaction with oxygen over a silver oxide catalyst. The ethylene oxide can then be converted into MEG. This may be carried out directly by catalytic or non-catalytic hydrolysis. Alternatively, in one well-known process ethylene oxide is catalytically reacted with carbon dioxide to produce ethylene carbonate. The ethylene carbonate is subsequently hydrolysed to provide ethylene glycol.

These routes rely for their starting material on ethylene, which is produced in the petrochemical industry by steam cracking of hydrocarbons derived from fossil fuels. In recent years increased efforts have been focussed on reducing the reliance on fossil fuels as a primary resource for the provision of fuels and commodity chemicals. Carbohydrates and related 'biomass' are seen as key renewable resources in the efforts to provide new fuels and alternative routes to desirable chemicals.

In particular, certain carbohydrates can be reacted with hydrogen in the presence of a catalyst system to generate polyols and sugar alcohols. Current methods for the conversion of saccharides to glycols revolve around a hydrogenation/hydrogenolysis process. A process for the conversion of cellulose to products including MEG is described in Angew. Chem. Int. Ed. 2008, 47, 8510-8513. Continuous processes for generating at least one polyol from a saccharide-containing feedstock are described in WO 2013/015955 and CN 103731258A.

The products of these reactions are a mixture of materials comprising MEG, monopropylene glycol (MPG), 1,2-butanediol (1,2-BDO) and other by-products. Although the conversion of glucose to glycols can be carried out with high selectivity to MEG, a much lower selectivity and increased levels of MPG are obtained when using sucrose as a feedstock. MPG has a much more limited market demand than MEG. However, from an economic point of view, sucrose would be a more desirable starting material for this process.

It would be desirable to provide a process for the production of MEG from a bio-based feedstock in which the selectivity to MEG was increased and fewer, or more desirable, by-products were produced.

SUMMARY OF THE INVENTION

Accordingly, the present invention provides a process for the preparation of monoethylene glycol from sucrose comprising the steps of:
i) hydrolysing sucrose to form a reaction product stream comprising glucose and fructose;
ii) separating the reaction product stream comprising glucose and fructose into a fructose or fructose derivative rich stream and a glucose rich stream; and
iii) contacting the glucose rich stream with hydrogen in a reactor in the presence of a solvent and a catalyst system with catalytic hydrogenation abilities to produce a product stream comprising MEG.

DETAILED DESCRIPTION OF THE INVENTION

Figure 1:
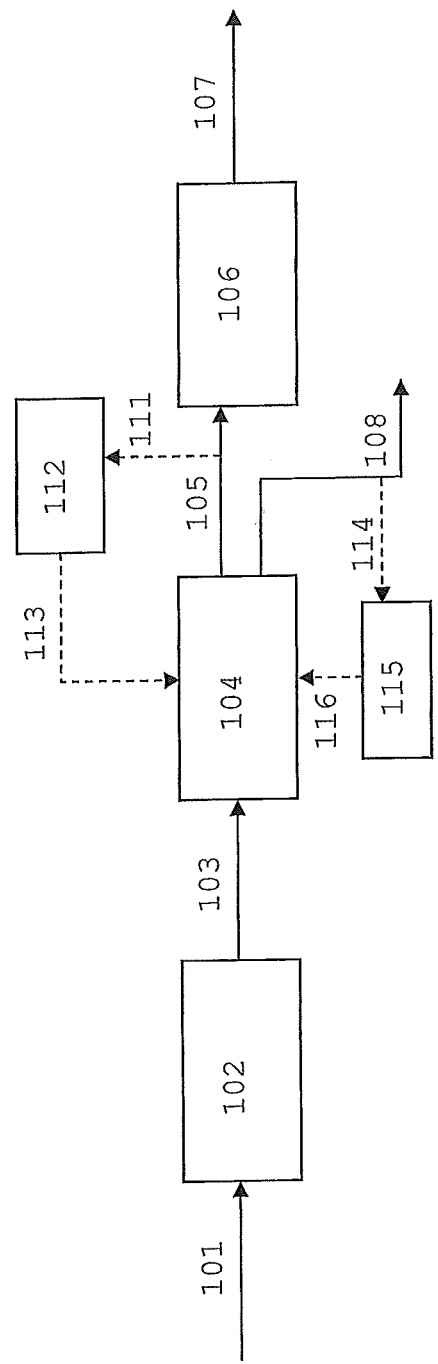
FIGS. 1 and 2 are schematic diagrams of exemplary, but non-limiting, embodiments of the process of the invention.

The present inventors have surprisingly found that a highly flexible process for the production of MEG with moderate co-production of MPG can be carried out using sucrose as the feed stock. The sucrose is hydrolysed to form glucose and fructose which are then separated. The glucose is then supplied to a hydrogenolysis/hydrogenation reaction in order to form MEG with low MPG co-production. The separated fructose rich stream can then be used directly, recycled or converted to key chemical building blocks in order to provide an efficient and flexible overall process.

Sucrose is a disaccharide in which a molecule of glucose and a molecule of fructose are joined by a glycosidic bond. Hydrolysis of this bond results in the production of the glucose and fructose as individual molecules. Such hydrolysis may be carried out in the process of the invention by any suitable process. In one embodiment, the hydrolysis may be carried out enzymatically, for example with a sucrase such as invertase. In another embodiment of the invention, hydrolysis may be carried out by chemical means, for example by using an acid such as hydrochloric acid.

Separation of the reaction product stream into a glucose rich stream and a fructose rich stream may also be carried out by any suitable method. One well-known method for the separation of glucose and fructose is the use of simulated moving-bed chromatography as described in Chemtech, 1997, 27(9), 36.

Depending on the method of separation used, the glucose rich stream will preferably less than 25 wt %, more preferably less than 10 wt %, most preferably contain less than 5 wt % fructose based on the weight of glucose and fructose in the overall stream.

Depending on the method of separation used, the fructose or fructose derivative rich stream will preferably contain less than 25 wt %, more preferably less than 10 wt %, most preferably less than 5 wt % glucose based on the weight of glucose and fructose in the overall stream.

In an alternative embodiment of the invention, separation of glucose and fructose may be carried out by reacting the fructose in the presence of the glucose, under conditions milder than those required for the conversion of the glucose, to form one or more fructose derivative. The reaction product stream from this reaction will comprise glucose and one or more fructose derivatives. Separation into a glucose rich stream and a fructose derivative rich stream may then be carried out.

In a preferred embodiment of the invention, fructose in the reaction product stream comprising glucose and fructose is selectively converted to hydroxylmethylfurfural (HMF) and/or alkoxy anologues thereof before the stream is subjected to separation. This may be carried out in an aqueous or an organic solvent or in a biphasic aqueous/organic solvent mixture at mild temperature and acidity. Examples of suitable methods may be found in Chem. Rev., 2013, 113, 1499 and Starch, 1990, 42(8), 314.

The subsequent separation of the reaction product mixture into a glucose rich stream and a fructose derivative rich stream may be carried out by a solvent extraction method. For example, HMF may be extracted from an aqueous medium by an organic solvent such as methyl isobutyl ketone (MIBK) or glucose may be extracted from an organic medium using an aqueous solvent.

The separated fructose or fructose derivative rich stream can be used in a multitude of ways in order to increase the flexibility of the process and desirability of the product slate obtainable therefrom.

In one embodiment of the invention the fructose rich stream will be used, optionally after further purification, as a sweetener in food or drink. Fructose has a relative sweetness of 180, compared with 100 for sucrose, making it a high value product as a sweetener.

In a further embodiment of the invention, the fructose rich stream may be subjected to an isomerisation reaction to convert it to a stream comprising a mixture of glucose and fructose. Said stream comprising a mixture of glucose and fructose may then be recycled and combined with the reaction product stream comprising glucose and fructose (from the sucrose hydrolysis) before it is separated into a glucose-rich stream and a fructose-rich stream. This embodiment allows conversion of the whole of the sucrose molecule into MEG with low MPG co-production via glucose rather than using fructose as part of the starting material in the hydrogenation/hydrogenolysis reaction. Glucose is known to produce MEG in a more selective manner than fructose.

Any suitable method for the isomerisation of fructose to glucose may be used. Both enzymatic and chemical processes for this transformation have been described in the art. See, for example Proc. Natl. Acad. Sci. USA, 2010, 107(14), 6164; Recl. Tray, Chim, Pay-Bas, 1984, 103, 361; and J. Am. Chem. Soc., 1960, 82, 4975.

In another embodiment of the invention, the fructose present in the fructose rich stream may be converted to hydroxymethylfurfural (HMF) or an analogue thereof such as an alkoxymethylfurfural. For instance, when the reaction is carried out in the presence of alcohols, diols or olefins, the product mixture will contain an alkoxymethylfurfural besides HMF. Examples of this can be seen in EP2033958, WO2009/30504 and WO2009/30508.

HMF and its analogues are important building blocks in the production of many other valuable chemical compounds. The HMF may be further converted into, for example, levulinic acid, 2,5-furandicarboxylic acid (FDCA), 5-alkoxymethylfurfural, caprolactam, caprolactone, 1,6-hexanediol, adipic acid, bis(5-methylfurfuryl)ether, 2,5-dimethylfuran, bishydroxymethylfuran, 5-hydroxymethylfuroic acid as well as their ring-hydrogenation products. Details of these products and their production from HMF can be found in Chem. Rev. 2013, 113, 1499-1597 and Starch, 1990, 42(8), 314.

Further, HMF, its analogues and derivatives may also be converted into important components of biofuels such as dimethylfuran, dimethyl tetrahydrofuran, levulinate esters, valerate esters, pentenoates esters, as well as kerosene- and diesel-range hydrocarbons produced by condensation of HMF with ketones and subsequent hydrodeoxygenation.

In a further embodiment of the invention, the fructose may be used in the direct production of levulinic acid by acid-catalysed dehydration in water.

In a particularly preferred embodiment of the invention, the fructose is converted into HMF and subsequently into FDCA. FDCA and MEG are the key building blocks in polyethylene furanoate (PEF), a polyethylene terephthalate alternative manufactured from bio-based materials. In this embodiment of the invention, the necessary building blocks for a totally bio-based plastic are provided from a single source in an efficient manner.

It is also an embodiment of the present invention to convert the HMF to bio-based terephthalic acid, allowing the production of the key building blocks of PET from bio-based materials.

After separation of the reaction product stream comprising glucose and fructose into a fructose or fructose derivative rich stream and a glucose rich stream, the glucose rich stream is contacted with hydrogen in a reactor in the presence of a solvent and a catalyst system with catalytic hydrogenation abilities to produce a product stream comprising MEG.

The solvent present in the reactor may be water or a $C_1$ to $C_6$ alcohol or mixtures thereof. Preferably, the solvent is water.

The catalyst system used preferably comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

Preferably, the first active catalyst component consists of one or more of the group selected from iron, cobalt, nickel, ruthenium, rhodium, palladium, iridium and platinum. This component may be present in the elemental form or as a compound. It is also suitable that this component is present in chemical combination with one or more other ingredients in the catalyst system. It is required that the first active catalyst component has catalytic hydrogenation capabilities and it is capable of catalysing the hydrogenation of material present in the reactor.

Preferably, the second active catalyst component comprises of one or more compound, complex or elemental material comprising tungsten, molybdenum, vanadium, niobium, chromium, titanium or zirconium. More preferably the second active catalyst component comprises one or more material selected from the list consisting of tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. Preferably, the second active catalyst component comprises one or more compound, complex or elemental material selected from those containing tungsten or molybdenum.

The catalyst components may be heterogeneous or homogeneous with respect to the solvent or solvents present in the reactor during the process of the present invention. The catalyst components may be preloaded into the reactor or, if they are in liquid form or present as a solution or slurry in a solvent, they may be fed into the reactor as required in a continuous or discontinuous manner during the process of the present invention.

Preferably, at least one of the active catalyst components is supported on a solid support. In this embodiment, any other active catalyst component may be present in either heterogeneous or homogeneous form. Said any other active catalyst component may also be supported on a solid support. In one embodiment, the first active catalyst component is supported on one solid support and the second active catalyst component is supported on a second solid support which may comprise the same or different material. In another embodiment, both active catalyst components are supported on one solid support.

The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Suitably, the weight ratio of the first active catalyst component to the second active catalyst component is in the range of from 0.02:1 to 3000:1, preferably in the range of from 0.1:1 to 100:1, on the basis of the weight of metal present in each component.

The weight ratio of the first active catalyst component (based on the amount of metal in said component) to sugar is suitably in the range of from 1:100 to 1:10000. The weight ratio of the second active catalyst component (based on the amount of metal in said component) to sugar is suitably in the range of from 1:10 to 1:1000.

The temperature in the reactor is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the reactor is heated to a temperature within these limits before addition of any starting material and is maintained at such a temperature until all reaction is complete.

The pressure in the reactor is suitably at least 1 MPa, preferably at least 2 MPa, more preferably at least 3 MPa. The pressure in the reactor is suitably at most 12 MPa, preferably at most 10 MPa, more preferably at most 8 MPa, even more preferably at most 6 MPa. Preferably, the reactor is pressurised to a pressure within these limits by addition of hydrogen before addition of any starting material and is maintained at such a pressure until all reaction is complete. This can be achieved by subsequent addition of hydrogen.

Contacting the glucose rich stream with hydrogen preferably takes place in the absence of air or oxygen. In order to achieve this, it is preferable that the atmosphere in the reactor be evacuated and replaced with hydrogen repeatedly, after loading of any initial reactor contents. It may also be suitable to add further hydrogen to the reactor as the reaction proceeds.

The reactor in which the glucose rich stream is contacted with hydrogen may be any suitable reactor known in the art.

Embodiments of the invention are now described by way of example only and with reference to the accompanying non-limiting figures.

In FIG. 1, a feed 101 comprising sucrose is provided to hydrolysis reactor 102 producing a reaction product stream 103 comprising glucose and fructose. Said reaction product stream 103 is separated in separation process 104 to provide a glucose rich stream 105 and a fructose or fructose derivative rich stream 108. The glucose rich stream undergoes hydrogenation/hydrogenolysis in reactor 106 to produce a product stream comprising MEG 107.

Optionally (indicated by dashed lines in FIG. 1) in this embodiment, at least a portion of one of the glucose rich stream 105 or the fructose rich stream 108 may be separated to provide streams 111 and 114, respectively, which are then provided to an isomerisation step (112 and 115, respectively) and the resultant streams (113 and 116) are provided back to the separation step 104 or to the reaction product stream 103 comprising glucose and fructose (not indicated on FIG. 1). This embodiment provides flexibility to increase or decrease the ratio of MEG:fructose and, therefore, the ratio of MEG:fructose derivative being produced in the process allowing it to be tailored to, for example, the production of PEF from MEG and FDCA.

In one example of this embodiment of the invention, the whole of stream 105 may be recycled via an isomerisation step 112 and the resultant stream 113 is provided back to the separation step. This embodiment would allow all of the sucrose to be converted to fructose and/or fructose derivatives, such as HMF and FDCA, thus allowing further tailoring of the overall process to a desired product slate.

Figure 2:
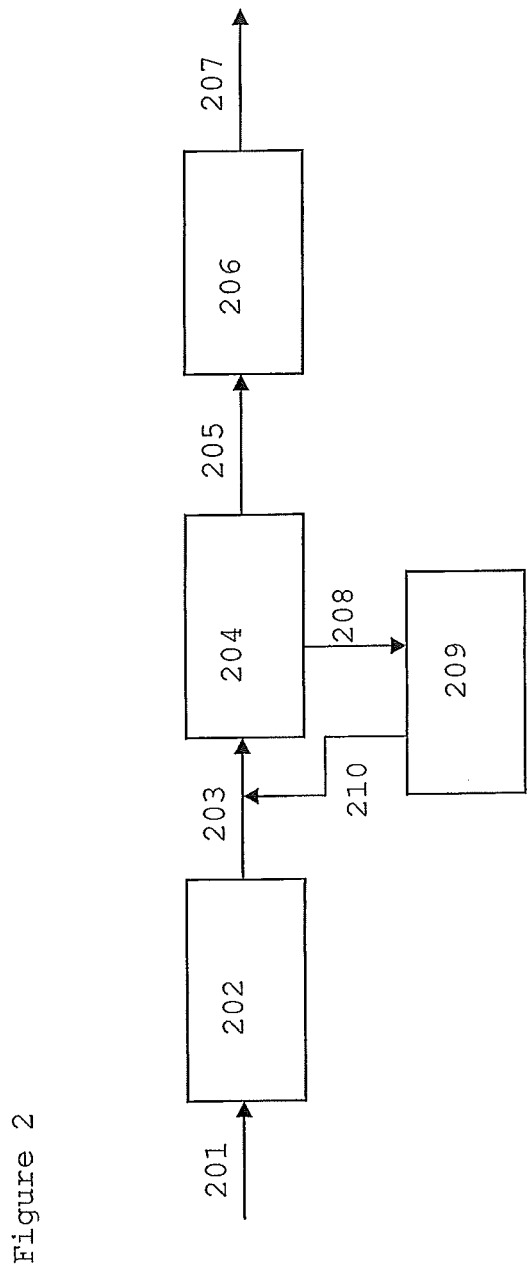

An alternative embodiment is exemplified in FIG. 2 in which a feed 201 comprising sucrose is provided to hydrolysis reactor 202 producing a reaction product stream 203 comprising glucose and fructose. Said reaction product stream 203 is separated in separation process 204 to provide a glucose rich stream 205 and a fructose or fructose rich stream 208. The glucose rich stream undergoes hydrogenation/hydrogenolysis in reactor 206 to produce a product stream comprising MEG 207.

The fructose rich stream is subjected to isomerisation in reactor 209 to produce a stream 210 comprising fructose and glucose, which is then recycled to stream 203.

It is envisaged that the hydrolysis step 202 and glucose/fructose isomerisation in 209 could be combined in the same reactor to further simplify the process.

The present invention is further illustrated in the following Examples.

EXAMPLES

Example 1

0.3 g glucose dissolved in 30 ml deionized water, 0.025 g of a W(10.88)-Ni(3.63)-Pt(0.05)/$ZrO_2$ catalyst and 0.025 g of a Ru(1.0)/$SiO_2$ catalyst were charged into a 60 ml autoclave, equipped with a gas stirrer and hydrogen supply. The autoclave was closed, the gas phase replaced by nitrogen, then by hydrogen and the autoclave was then pressurised to 30 bara pressure. The autoclave was stirred at 1450 rpm, heated to 195° C. in 12-15 minutes and kept at 195° C. and 85 bara for 75 minutes. The reactor was then cooled to room temperature in 15 minutes, depressurized, opened and a liquid sample of 0.3 ml was taken for analysis.

Yields of MEG, MPG and 1,2-butanediol (1,2-BDO) were quantified by GC-FID, applying a CPSil-5 column.
Glycols yields are shown in Table 1.

Examples 2 and 3

Example 1 was repeated twice. In Example 2, glucose was replaced with fructose. In Example 3 glucose was replaced with sucrose.
Glycol yields are shown in Table 1.

| Example | Carbohydrate | MEG (% wt) | MPG (% wt) | 1,2-BDO (% wt) |
|---|---|---|---|---|
| 1 | Glucose | 42.9 | 11.7 | 4.8 |
| 2 | Fructose | 6.1 | 3.9 | 1.7 |
| 3 | Sucrose | 30.0 | 21.9 | 3.8 |

What is claimed is:

1. A process for the preparation of monoethylene glycol from sucrose comprising the steps of:
   i) hydrolysing sucrose to form a reaction product stream comprising glucose and fructose;
   ii) separating the reaction product stream comprising glucose and fructose into a fructose or fructose derivative rich stream and a glucose rich stream; and
   iii) contacting the glucose rich stream with hydrogen in a reactor in the presence of a solvent and a catalyst system with catalytic hydrogenation abilities to produce a product stream comprising monoethylene glycol.

2. A process according to claim 1, wherein the fructose rich stream resulting from step ii) is subjected to an isomerisation reaction to provide a further stream comprising fructose and glucose and this further stream is recycled and combined with the reaction product stream comprising glucose and fructose formed in step i).

3. A process according to claim 1, wherein the fructose rich stream is used, optionally after further purification, as a sweetener in food or drink.

4. A process according to claim 1, wherein the fructose rich stream undergoes reaction to transform at least a portion of the fructose therein to hydroxymethylfufural or an alkoxy analogue thereof.

5. A process according to claim 4, wherein the hydroxymethylfurfural is then converted to 2,5-furandicarboxylic acid.

6. A process according to claim 5, wherein the 2,5-furandicarboxylic acid and the monoethylene glycol are used to produce polyethylene furanoate.

7. A process according to claim 1, wherein the fructose rich stream undergoes reaction to transform at least a portion of the fructose therein to levulinic acid, optionally via conversion to hydroxymethylfurfural.

8. A process according to claim 1, wherein the separation in step ii) is carried out by first converting fructose to a fructose derivative using conditions under which at least 50 wt % of the glucose does not react and then by separating the thus-formed reaction product stream into a glucose rich stream and a fructose derivative rich stream.

9. A process for the conversion of sucrose into fructose and/or fructose derivatives comprising the steps of:
   i) hydrolysing sucrose to form a reaction product stream comprising glucose and fructose;
   ii) separating the reaction product stream comprising glucose and fructose into a fructose or fructose derivative rich stream and a glucose rich stream; and
   iii) subjecting the glucose rich stream to an isomerisation reaction to provide a further stream comprising fructose and glucose and recycling this further stream is recycled and combined with the reaction product stream comprising glucose and fructose formed in step i).

10. A process as claimed in claim 9, wherein the fructose rich stream undergoes reaction to transform at least a portion of the fructose therein to hydroxymethylfufural or an alkoxy analogue thereof.

* * * * *